(12) United States Patent
Tucker et al.

(10) Patent No.: US 10,512,659 B2
(45) Date of Patent: Dec. 24, 2019

(54) METHODS AND DEVICES FOR PREPARATION OF ENRICHED BIOLOGICAL FLUIDS

(71) Applicant: Arthrex, Inc., Naples, FL (US)

(72) Inventors: Melissa D. Tucker, Naples, FL (US); Christopher Bare, Naples, FL (US); Abigail Nabors, Naples, FL (US); Robert Harrison, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 15/201,395

(22) Filed: Jul. 2, 2016

(65) Prior Publication Data

US 2017/0000826 A1    Jan. 5, 2017

Related U.S. Application Data

(60) Provisional application No. 62/188,118, filed on Jul. 2, 2015.

(51) Int. Cl.

| | |
|---|---|
| *A61K 35/19* | (2015.01) |
| *A61M 1/36* | (2006.01) |
| *A61K 35/28* | (2015.01) |
| *A61K 9/00* | (2006.01) |
| *B01D 17/02* | (2006.01) |
| *B01D 21/26* | (2006.01) |
| *A61K 35/16* | (2015.01) |
| *A61M 1/38* | (2006.01) |
| *A61M 1/02* | (2006.01) |
| *A61K 35/12* | (2015.01) |

(52) U.S. Cl.
CPC ............ *A61K 35/19* (2013.01); *A61K 9/0019* (2013.01); *A61K 35/16* (2013.01); *A61K 35/28* (2013.01); *A61M 1/029* (2013.01); *A61M 1/3693* (2013.01); *A61M 1/382* (2013.01); *B01D 17/0217* (2013.01); *B01D 21/262* (2013.01); *A61K 2035/124* (2013.01); *A61M 2202/0427* (2013.01); *A61M 2202/0437* (2013.01); *A61M 2202/08* (2013.01); *A61M 2202/10* (2013.01)

(58) Field of Classification Search
CPC ......... A61M 1/36; A61M 1/382; A61K 35/19; A61K 35/28
USPC ........................................................... 435/2
See application file for complete search history.

(56) References Cited

U.S. PATENT DOCUMENTS

| | | |
|---|---|---|
| 6,716,187 B1 | 4/2004 | Jorgensen |
| 7,452,344 B2 | 11/2008 | Jorgensen |
| 7,927,563 B1 | 9/2011 | Lavi |
| 8,052,969 B2 | 11/2011 | Buhr |
| 8,950,586 B2 | 2/2015 | Dorian et al. |
| 9,050,403 B2 | 6/2015 | Morimoto |
| 9,101,688 B2 | 8/2015 | Teets et al. |
| 9,205,110 B2 | 12/2015 | Bare |
| 9,241,977 B2 | 1/2016 | Bare et al. |
| 9,329,165 B2 | 5/2016 | Ihm |
| 9,555,171 B2 | 1/2017 | Sengun |
| 9,718,003 B1 | 8/2017 | Petrie |
| 9,757,506 B2 | 9/2017 | Ra |
| 9,804,070 B2 | 10/2017 | Hassouneh |
| 10,040,064 B1 | 8/2018 | Petrie |
| 10,058,799 B2 | 8/2018 | Lee |
| 2008/0166421 A1* | 7/2008 | Buhr ............... A61K 35/18 424/530 |
| 2012/0237490 A1 | 9/2012 | Karli |
| 2014/0010857 A1 | 1/2014 | Turzi et al. |
| 2014/0272925 A1 | 9/2014 | Menon |
| 2015/0064687 A1* | 3/2015 | Nemirovsky ...... A61M 1/029 435/2 |
| 2015/0209502 A1 | 7/2015 | Bare |
| 2015/0328388 A1* | 11/2015 | Okamoto .......... A61M 1/02 210/805 |
| 2016/0008808 A1 | 1/2016 | Levine |
| 2017/0028137 A1 | 2/2017 | Mirabito |
| 2017/0144173 A1 | 5/2017 | Sengun |
| 2018/0106706 A1 | 4/2018 | Hassouneh |
| 2018/0120206 A1 | 5/2018 | Hassouneh |
| 2018/0264199 A1 | 9/2018 | Mirabito |

FOREIGN PATENT DOCUMENTS

| | | |
|---|---|---|
| CA | 2617465 A1 | 7/2009 |
| EP | 2823832 A1 | 1/2015 |
| WO | 2017093838 A1 | 6/2017 |

OTHER PUBLICATIONS

International Search Report and Written Opinion for corresponding PCT application No. PCT/US2016/040890 dated Oct. 17, 2016.
Simari et al., "Bone marrow mononuclear cell therapy for acute myocardial infarction: A perspective from the cardiovascular cell therapy research network", Circulation Research, 114:1564-1568 (2014).
Rodriguez et al., "Autologous stromal vascular fraction therapy for rheumatoid arthritis: rationale and clinical safety", International Archives of Medicine, 5(5):1-9 (2012).
Song, et al. "Comparison of the efficacy of bone marrow mononuclear cells and bone mesenchymal stem cells in the treatment of osteoarthritis in a sheep model". Int J Clln Exp Pathol. vol. 7 No. 4, pp. 1415-1426, (2014).

* cited by examiner

*Primary Examiner* — Ruth A Davis
(74) *Attorney, Agent, or Firm* — DLA Piper LLP (US)

(57) ABSTRACT

The present disclosure relates to methods and apparatus for producing platelet rich plasma, bone marrow mononuclear cells, stromal vascular fraction from adipose tissue, and other concentrated or enriched biological fluids.

16 Claims, 3 Drawing Sheets

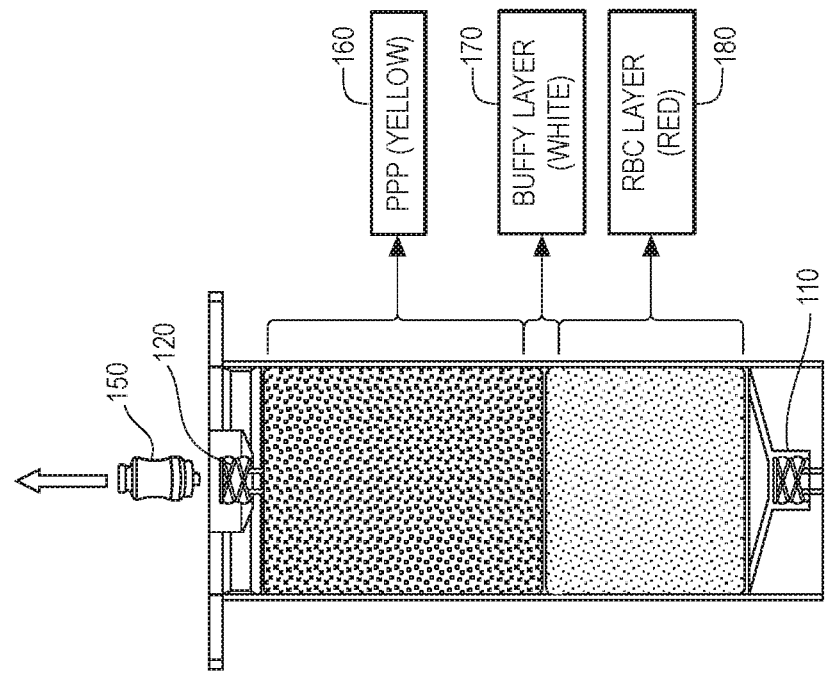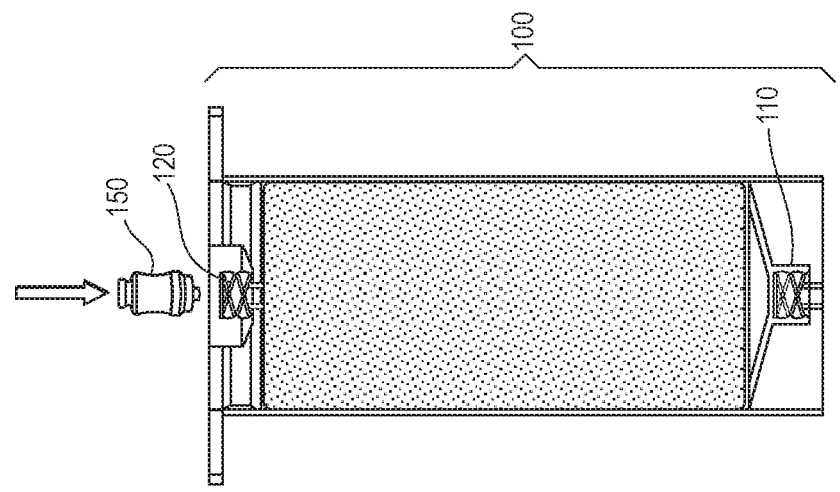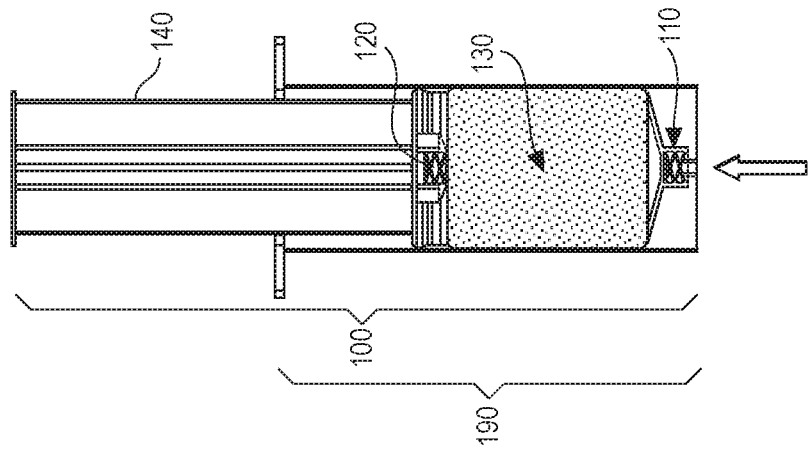

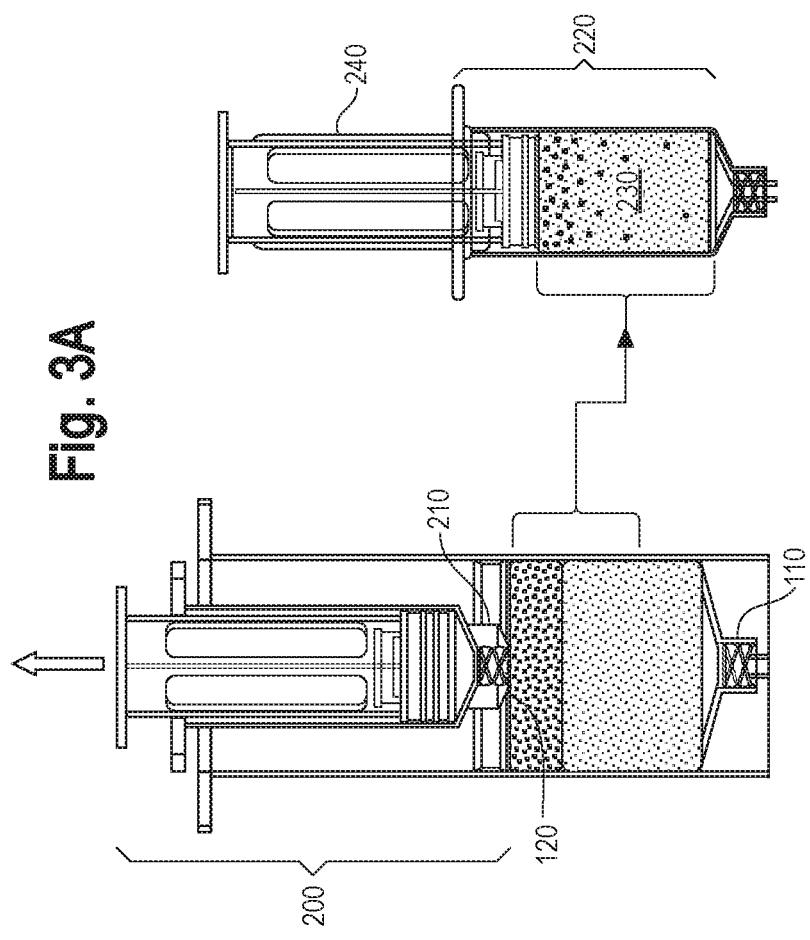

METHODS AND DEVICES FOR PREPARATION OF ENRICHED BIOLOGICAL FLUIDS

PRIORITY

This application claims the benefit of U.S. Ser. No. 62/188,118, filed on Jul. 2, 2015, which is incorporated by reference herein in its entirety.

BACKGROUND

The present disclosure relates to methods and apparatus for producing platelet rich plasma, bone marrow mononuclear cells (BMMC), stromal vascular fraction (SVF) from adipose tissue, and other enriched or concentrated biological fluids. The present disclosure also discloses methods for treating damaged tissue with platelet rich plasma, bone marrow mononuclear cells, a stromal vascular fraction of adipose tissue, or other enriched or concentrated biological fluid, and a platelet rich plasma, bone marrow mononuclear cells, a stromal vascular fraction of adipose tissue, or other enriched or concentrated biological fluid for use in the treatment of damaged tissues.

SUMMARY

Platelet rich plasma (PRP), bone marrow mononuclear cells (BMMC), a stromal vascular fraction (SVF) of adipose tissue, and other enriched or concentrated biological fluids and methods of generating these fluids are disclosed herein. An embodiment provides methods of whole blood fractionation. In an embodiment, whole blood can be fractionated into an erythrocyte layer, a buffy layer, and a platelet poor plasma (PPP) layer. In an embodiment, fractionation of whole blood can be achieved by centrifugation. At least a portion of the PPP layer can be removed, and the remaining fluid transferred to a different container. In an embodiment, the remaining fluid is transferred to a second container such as a double syringe. The remaining fluid can then be fractionated into two layers, an erythrocyte layer and a plasma layer (i.e., platelet rich plasma). In an embodiment, platelet rich plasma is removed from the second syringe or container and administered to a subject.

In an embodiment, a PRP produced by methods described herein comprises about $8 \times 10^6$ to about $1 \times 10^7$ platelets/μL. In an embodiment, a PRP produced by methods herein comprises about $0.1 \times 10^5$ to about $2 \times 10^5$ erythrocytes/μL. In an embodiment, a PRP produced by methods herein comprises about 500 to about 4000 white blood cells/μL. In an embodiment, a PRP produced by methods herein comprises about 10 to about 300 neutrophils/μL. A PRP in accordance with any of these embodiments of the invention may be employed in the medical uses described herein.

Other systems for generating PRP are known, but they do not provide a high concentration of platelets and can often produce PRP contaminated with unacceptably high concentrations of red blood cells, neutrophils, or white blood cells. The methods, medical uses, and compositions presented herein provide PRP with a high concentration of platelets and low concentrations of red blood cells, white blood cells, and neutrophils. The devices and methods disclosed herein can also be used to produce bone marrow mononuclear cells, stromal vascular fraction of adipose tissue, and other enriched or concentrated biological fluids.

An embodiment provides methods of bone marrow fractionation. The methods can comprise adding bone marrow to a first syringe having a top coupling element and a bottom coupling element and centrifuging the first syringe, wherein the bone marrow fractionates into a platelet poor plasma layer, a buffy layer, and an erythrocyte/granulocyte layer within the first syringe. Optionally, at least a portion of the platelet poor plasma layer can be removed from the top coupling element of the first syringe. A bottom coupling element of a second syringe or second container can be attached to the top coupling element of the first syringe. Any of the platelet poor plasma layer and the buffy layer can be drawn into the second syringe or second container. The second syringe or second container can be centrifuged wherein the platelet poor plasma layer and the buffy layer fractionates into a bone marrow mononuclear cell layer and an erythrocyte/granulocyte layer. BMMCs in accordance with any of these embodiments of the invention may be employed in the medical uses described herein. An embodiment provides a composition comprising blood marrow mononuclear cells produced by methods herein for use in the treatment of soft tissue injury or damage.

An embodiment provides methods of adipose tissue fractionation. The methods can comprise centrifuging adipose tissue in a first syringe having a top coupling element and a bottom coupling element, wherein the adipose tissue fractionates (top to bottom) into a lipid layer, an compressed adipose layer, and an excess fluid layer within the first syringe. At least a portion of the lipid layers and excess fluid layers can be removed from the top coupling element and the bottom coupling element, respectively, of the first syringe. A bottom coupling element of a second syringe can be attached to the top coupling element of the first syringe. The compressed adipose layer can be drawn into the second syringe or second container. The second syringe can be centrifuged wherein the compressed adipose layer fractionates into a top adipocyte layer and a bottom stromal vascular fraction. Embodiments provide a composition comprising the stromal vascular fraction produced by the methods herein for use in the treatment of soft tissue injury or damage. A SVF in accordance with any of these embodiments of the invention may be employed in the medical uses described herein.

BRIEF DESCRIPTION OF THE FIGURES

FIG. 2A-C shows use of a first syringe to generate PPP, buffy layer, and red blood cell layer.

FIG. 3A-B shows use of a first syringe and a second syringe to generate PRP.

DETAILED DESCRIPTION

Figure 1:
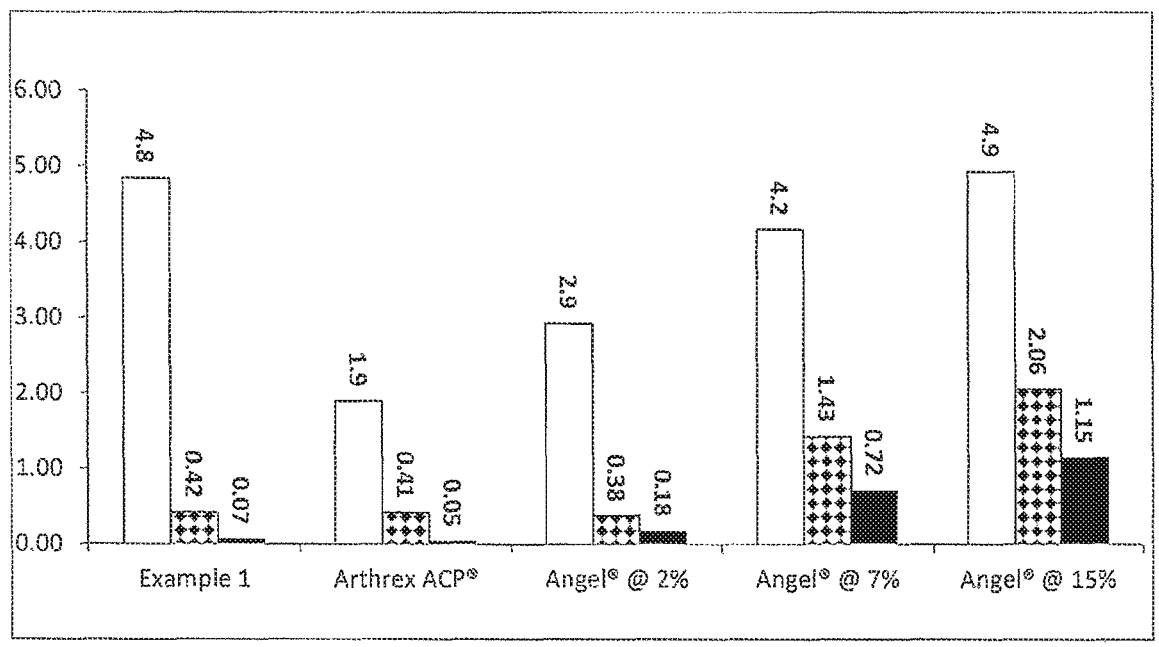
FIG. 1 is a graph depicting the platelet ratio (□), white blood cell ratio (♦), and neutrophil ratio (■) of the PRP generated by the method of Example 1, Arthrex ACP® double syringe system, Angel® PRP system at 2% hematocrit, Angel® PRP system at 7% hematocrit, and Angel® PRP system at 15% hematocrit when compared to the whole blood sample from the same donor.

Disclosed herein is concentrated platelet rich plasma (PRP), bone marrow mononuclear cells (BMMC), stromal vascular fraction (SVF) of adipose tissue, and other enriched or concentrated biological fluids and methods of generating these fluids. For platelet rich plasma, whole blood can be fractionated by centrifugation into a clear platelet poor plasma (PPP) fraction that is the top layer, a red erythrocyte fraction that is the bottom layer, and a whitish fraction between the top and bottom layers. The middle fraction is the "buffy layer", which contains most of the leukocytes, platelets, and mesenchymal and/or hematopoietic stem cells. FIG. 2C.

An embodiment provides methods of whole blood fractionation. Whole blood from a subject can be obtained by a phlebotomy needle, central vein catheter (e.g., a PICC line), or any other whole blood collection means. Other biological fluids can be obtained using any acceptable method. In an embodiment, whole blood can optionally be mixed with anticoagulants such as, for example, citrate, acid-citrate dextrose (ACD), citrate-phosphate-dextrose (CPD), or ethylene diamine tetra-acetic acid (EDTA). Heparin can also be added in an amount sufficient to prevent or inhibit thrombin activity during the processing steps. Proteolytic enzyme inhibitors, such as aprotinin, ε-aminocaproic acid, or tranexamic acid can be added to prevent proteolytic degradation of autogenous growth factors.

Centrifugation conditions (e.g., relative centrifugal force (RCF), time, etc.) determine the extent and degree of blood or other biological fluid fractionation. In an embodiment, a method of fractionating whole blood or other biological fluid includes centrifuging whole blood twice, wherein the first centrifugation is a hard spin and the second centrifugation is a soft spin. In an embodiment, a method of fractionating whole blood or other bodily fluid includes centrifuging whole blood twice, wherein the first centrifugation is a soft spin and the second centrifugation is a hard spin. In an embodiment, the hard spin is greater than 2000×g or from about 1500×g to about 2000×g. In an embodiment a soft spin is from about 30×g to about 200×g.

In an embodiment, a method of fractionating whole blood includes centrifuging whole blood twice, wherein the first centrifugation separates the blood into three fractions—the platelet poor plasma layer, the buffy layer, and the erythrocyte layer; and the second centrifugation separates the blood into two layers—a platelet rich plasma layer and an erythrocyte layer. A first centrifugation can be about 5 minutes to about 20 minutes in duration. A second centrifugation can be about 5 minutes to about 20 minutes in duration.

In an embodiment, whole blood can be centrifuged at a relative centrifugal force that is less than 2000×g but still fractionates the blood into a platelet poor plasma layer, a buffy layer, and an erythrocyte layer (e.g., a hard spin). In an embodiment, a whole blood sample can be centrifuged at about 1500×g, about 1550×g, about 1600×g, about 1650×g, about 1675×g, about 1700×g, about 1725×g, about 1750×g, about 1775×g, about 1800×g, about 1825×g, about 1850×g, about 1875×g, about 1900×g, about 1925×g, about 1950×g, or about 1975×g. In an illustrative embodiment, a whole blood sample can be centrifuged at a RCF of about 1500×g up to 2000×g, about 1550×g up to 2000×g, about 1600×g up to 2000×g, about 1650×g up to 2000×g, about 1675×g up to 2000×g, about 1700×g up to 2000×g, about 1725×g up to 2000×g, about 1750×g up to 2000×g, about 1775×g up to 2000×g, about 1800×g up to 2000×g, about 1825×g up to 2000×g, about 1850×g up to 2000×g, about 1875×g up to 2000×g, about 1900×g up to 2000×g, about 1925×g up to 2000×g, about 1950×g up to 2000×g, or about 1975×g up to 2000×g.

In an illustrative embodiment, a whole blood sample can be centrifuged at a RCF of about 1500×g to about 1900×g, about 1550×g to about 1900×g, about 1600×g to about 1900×g, about 1650×g to about 1900×g, about 1675×g to about 1900×g, about 1700×g to about 1900×g, about 1725×g to about 1900×g, about 1750×g to about 1900×g, about 1775×g to about 1900×g, about 1800×g to about 1900×g, about 1825×g to about 1900×g, about 1850×g to about 1900×g, or about 1875×g to about 1900×g (e.g., a hard spin).

In an illustrative embodiment, a whole blood sample can be centrifuged at a RCF of about 1500×g to about 1800×g, about 1550×g to about 1800×g, about 1600×g to about 1800×g, about 1650×g to about 1800×g, about 1675×g to about 1800×g, about 1700×g to about 1800×g, about 1725×g to about 1800×g, about 1750×g to about 1800×g, about 1775×g to about 1800×g, about 1650×g to about 1750×g, about 1675×g to about 1750×g, about 1700×g to about 1750×g, about 1675×g to about 1725×g, or about 1700×g to about 1725×g (e.g., a hard spin).

In an embodiment, a blood sample, such as a blood sample that has been subjected to a hard spin, can be centrifuged at a RCF that is less than 200×g and fractionates the blood into a plasma layer and an erythrocyte layer (e.g., a soft spin). In an illustrative embodiment, the plasma layer is a platelet rich plasma layer. In an embodiment, a blood sample can be centrifuged at about 30×g, about 35×g, about 40×g, about 45×g, about 50×g, about 55×g, about 60×g, about 70×g, about 75×g, about 80×g, about 90×g, about 100×g, about 110×g, about 120×g, about 125×g, about 150×g, about 175×g, or about 200×g.

In an illustrative embodiment, blood can be centrifuged at a RCF of about 30×g to about 200×g, about 30×g to about 175×g, about 30×g to about 150×g, about 30×g to about 125×g, about 30×g to about 120×g, about 30×g to about 110×g, about 30×g to about 100×g, about 30×g to about 90×g, about 30×g to about 80×g, about 30×g to about 75×g, about 30×g to about 70×g, about 30×g to about 60×g, about 30×g to about 50×g, about 30×g to about 45×g, about 40×g to about 200×g, about 40×g to about 175×g, about 40×g to about 150×g, about 40×g to about 125×g, about 40×g to about 120×g, about 40×g to about 110×g, about 40×g to about 100×g, about 40×g to about 90×g, about 40×g to about 80×g, about 40×g to about 75×g, about 40×g to about 70×g, about 40×g to about 60×g, about 40×g to about 50×g, or about 40×g to about 45×g (e.g., a soft spin).

In an embodiment, a first centrifugation (e.g., a hard spin) can be about 3, about 4, about 5, about 6, about 7, about 8, about 9, about 10, about 11, about 12, about 13, about 14, about 15, about 20, about 25, or about 30 minutes. In an embodiment, a second centrifugation (e.g., a soft spin) can be about 3, about 4, about 5, about 6, about 7, about 8, about 9, about 10, about 11, about 12, about 13, about 14, about 15, about 20, about 25, or about 30 minutes.

In an illustrative embodiment, at least a portion of the platelet poor plasma layer (PPP) can be removed after a first centrifugation (e.g., hard spin) and before a second centrifugation (e.g. a soft spin). In an embodiment, at least half, at least 75%, at least 80%, at least 85%, at least 90%, at least 95%, at least 98%, at least 99%, or 100% of the platelet poor plasma layer (PPP) is removed. The removed PPP can be saved for other purposes, such as diluting a final PRP preparation or used for creating an autologous clot.

Following removal of at least a portion of PRP, the remaining blood components can be transferred to a second container (e.g., a centrifuge tube or a syringe, e.g., an Arthrex ACP® double syringe system). In an embodiment, the PRP as disclosed herein is delivered into a syringe and is ready for immediate application.

In embodiments of the methods to produce PRP as described herein, the PRP comprises increased platelet levels compared to whole blood. In an embodiment, the PRP produced by methods herein comprise about $8\times10^6$ to about $1\times10^7$ platelets/µL. In an embodiment, the PRP produced by methods herein comprise about $8.5\times10^6$ to about $1 \times 10^7$ platelets/μL. In an illustrative embodiment, the PRP produced by methods herein comprise about $9 \times 10^6$ to about $1 \times 10^7$ platelets/μL. In an embodiment, the PRP produced by methods herein comprise about $9.5 \times 10^6$ to about $1 \times 10^7$ platelets/μL. In an embodiment, the PRP produced by methods herein comprise about $8 \times 10^6$, about $8.5 \times 10^6$, about $9 \times 10^6$, about $9.5 \times 10^6$, about $9.75 \times 10^6$, about $9.8 \times 10^6$, about $9.9 \times 10^6$, or about $1 \times 10^7$ platelets/μL.

In embodiments of the methods to produce PRP as described herein, the PRP comprises decreased erythrocyte (RBC) levels compared to whole blood. In an embodiment, the PRP produced by methods herein comprise less than about $2 \times 10^5$ RBC/μL, less than about $1.5 \times 10^5$ RBC/μL, less than about $1 \times 10^5$ RBC/μL, or less than about $0.5 \times 10^5$ RBC/μL.

In an embodiment, the PRP produced by methods herein comprises about $0.1 \times 10^5$ to about $2 \times 10^5$ RBC/μL, about $0.1 \times 10^5$ to about $1.5 \times 10^5$ RBC/μL, about $0.1 \times 10^5$ to about $1 \times 10^5$ RBC/μL, about $0.1 \times 10^5$ to about $0.75 \times 10^5$ RBC/μL, about $0.1 \times 10^5$ to about $0.6 \times 10^5$ RBC/μL, about $0.1 \times 10^5$ to about $0.5 \times 10^5$ RBC/μL, about $0.25 \times 10^5$ to about $1.5 \times 10^5$ RBC/μL, about $0.25 \times 10^5$ to about $1 \times 10^5$ RBC/μL, about $0.25 \times 10^5$ to about $0.75 \times 10^5$ RBC/μL, about $0.25 \times 10^5$ to about $0.6 \times 10^5$ RBC/μL, about $0.25 \times 10^5$ to about $0.5 \times 10^5$ RBC/μL, about $0.5 \times 10^5$ to about $1.5 \times 10^5$ RBC/μL, about $0.5 \times 10^5$ to about $1 \times 10^5$ RBC/μL, about $0.5 \times 10^5$ to about $0.75 \times 10^5$ RBC/μL, or about $0.5 \times 10^5$ to about $0.6 \times 10^5$ RBC/μL.

In embodiments of the methods to produce PRP as described herein, the PRP comprises decreased white blood cell (WBC) levels compared to whole blood. In an embodiment, the PRP produced by methods herein comprise less than about $4 \times 10^3$ WBC/μL, less than about $3.5 \times 10^3$ WBC/μL, less than about $3 \times 10^3$ WBC/μL, less than about $2.5 \times 10^3$ WBC/μL, less than about $2 \times 10^3$ WBC/μL, less than about $1.5 \times 10^3$ WBC/μL, less than about $1 \times 10^3$ WBC/μL, or less than about $0.5 \times 10^3$ WBC/μL.

In an embodiment, the PRP produced by methods herein comprises about 500 to about 4000 WBC/μL, about 500 to about 3500 WBC/μL, about 500 to about 3000 WBC/μL, about 500 to about 2500 WBC/μL, about 500 to about 2000 WBC/μL, about 500 to about 1500 WBC/μL, about 500 to about 1000 WBC/μL, about 500 to about 750 WBC/μL, or about 500 to about 550 WBC/μL, about 750 to about 3500 WBC/μL, about 1000 to about 3500 WBC/μL, about 750 to about 3000 WBC/μL, about 1000 to about 3000 WBC/μL, about 750 to about 2500 WBC/μL, or about 1000 to about 2500 WBC/μL.

In embodiments of the methods to produce PRP as described herein, the PRP comprises decreased neutrophil (N) levels compared to whole blood. In an embodiment, the PRP produced by methods herein comprise less than about 300 N/μL, about 250 N/μL, about 230 N/μL, about 225 N/μL, about 200 N/μL, about 175 N/μL, about 150 N/μL, about 125 N/μL, about 120 N/μL, about 110 N/μL, about 100 N/μL, about 75 N/μL, about 50 N/μL, about 25 N/μL, about 20 N/μL, about 15 N/μL, or about 10 N/μL.

In an embodiment, the PRP produced by methods herein comprises about 10 to about 300 N/μL, about 10 to about 250 N/μL, about 10 to about 230 N/μL, about 10 to about 225 N/μL, about 10 to about 200 N/μL, about 10 to about 175 N/μL, about 10 to about 150 N/μL, about 10 to about 125 N/μL, about 10 to about 120 N/μL, about 10 to about 100 N/μL, about 10 to about 75 N/μL, about 10 to about 50 N/μL, or about 10 to about 25 N/μL.

Devices

In an embodiment, a device for preparation of PRP can comprise a first syringe 100 having a bottom coupling element 110, for, e.g. direct attachment of an infusion set to draw blood directly into the first syringe. FIG. 2A. A coupling element can be a luer lock connector or any other type of small-scale fluid fitting for making leak-free connections between a male-taper fitting and its mating female part. The first syringe also can comprise a top coupling element 120. The top coupling element can be connected to, for example, a swabbable, needless injection luer connector 150 or a plunger 140. The first syringe can comprise a barrel 190 with a chamber 130 suitable for biological fluids. Biological fluid can be drawn up into the chamber 130 of the first syringe with a plunger 140 connected to the top coupling element 120 (or other suitable means).

A biological fluid, e.g., whole blood, can be drawn into the first syringe, either directly from the patient or from a container containing a previously collected sample of biological fluid. Any amount of biological fluid can be used, for example, about 10, 20, 50, 75, 100, 125, 150, 200, 300 or more mL. The plunger 140 can be removed from the top coupling element 120 and a swabbable needleless injector luer 150 (or other luer lock port or injector port) is placed into the top coupling element (FIG. 2B). The first syringe is placed into a centrifuge and spun under, for example, hard spin conditions. Three layers of biological fluids can be present after centrifugation: a PPP layer 160, a buffy layer 170, and a red blood cell or erythrocyte layer 180 (FIG. 2C).

Optionally, an amount of the PPP layer (e.g., about 1, 2, 5, 10, 20, 30, 40, 50 mL or more) can be removed via the swabbable needless injector luer 150 or top coupling element 120 leaving behind the desired volume of PPP (e.g., about 50, 40, 30, 20, 10, 5, 2, 1, or less mL). The optionally removed PPP can be used for, e.g., dilution of the PRP final injection or to make an autologous clot. Alternatively, all of the PPP can be retained in the first syringe. A second syringe 200 or other second container can be connected to the top coupling element 120 or swabbable needless injector luer 150. A second syringe can be an Arthrex ACP® double syringe. A double syringe comprises, for example, a distal (outer) syringe having a first body with a first diameter; and a proximal (inner) syringe having a second body with a second diameter smaller than the first diameter, the distal (outer) syringe being in direct fluid communication with the proximal (inner) syringe, and the proximal (inner) syringe being located within the distal (outer) syringe. A second syringe or other second container can have a bottom coupling element 210 and a plunger 240. The barrel 220 of the second syringe or second container can comprise a chamber 230 that can hold a biological fluid. The barrel of the second syringe or second container can have a smaller diameter than the first syringe so that the second syringe can fit within the barrel of the first syringe. See FIG. 3A.

All or part of the biological fluid present in the first syringe (e.g., PPP, buffy layer, red blood cell layer) can be drawn through the top coupling element 120 of the first syringe and into the second syringe 200 or other second container. FIG. 3A. In one example, the PPP layer, the buffy layer and optionally part of the red blood cell layer (e.g., about less than 1, 2, 5, 10, 15, or 30 mL) of the red blood cell layer can be drawn up into the second syringe or other second container. The second syringe or second container can be removed from the first syringe and placed into a centrifuge. The second syringe or second container can be centrifuged under, for example, soft spin conditions. Two layers can be present after the second centrifugation: a PRP layer 235 and an erythrocyte layer 240. FIG. 3B. The PRP layer can be isolated by, for example, expelling the erythrocyte layer from the bottom coupling element 210 of the second syringe or second container. The PPP can then be used for direct injection into the patient through an injection set connected to bottom coupling element 210 of the second syringe or second container or can be stored in the second syringe or second container for later use, or removed from the chamber of the second syringe or second container and stored in another container for later use.

Where the second container is a double syringe, such as an Arthrex ACP® double syringe, the plunger of the inner syringe can be used for easy isolation of PRP after the second centrifugation. The inner syringe (of the double syringe) can be pulled up to isolate the PRP after the second centrifugation. Therefore, the inner syringe of the second, double syringe can be used to pull up the PRP without disturbing the RBC layer. The inner syringe of the second syringe can then be removed, a needle can be attached to the bottom coupling element, and the inner syringe of the second, double syringe can be used to directly inject the PRP into a patient or container.

Other Uses of Devices

The devices and methods described herein can be used with other biological fluids including, for example, bone marrow or adipose tissue.

An embodiment provides methods of bone marrow fractionation. In an embodiment bone marrow mononuclear cells (BMMC) can be isolated. BMMCs are a mixed population of single nucleus cells including monocytes, lymphocytes, and hematopoietic and/or mesenchymal stem cells and progenitor cells. Bone marrow, bone marrow aspirate, or bone marrow concentrate (i.e., a bone marrow sample) can be can be drawn up into the chamber 130 of a first syringe with a plunger 140 connected to a top coupling element 120. The bone marrow sample can be drawn into the first syringe, either directly from the patient or from a container containing a previously collected sample of bone marrow. A density gradient medium (e.g. Percoll or Ficoll at a p of about 1.070 to about 1.080) can optionally be drawn into the first syringe such that the bone marrow sample is a top layer and the density gradient medium is a bottom layer in the chamber of the first syringe. Alternatively, the density gradient medium can be drawn up into the first syringe through the bottom coupling element 110 and then the bone marrow sample added through the top coupling 120 element of the first syringe. The plunger 140 (if used) can be removed from the top coupling element and a swabbable needleless injector luer 150 (or other luer lock port or injector port) can be placed into the top coupling element 120. FIG. 2A. The first syringe can be placed into a centrifuge and spun under, for example, any of the hard spin centrifuge conditions described above for isolation of PRP, for example at about 2000×g for about 10 minutes. Three or four layers of biological fluids can be present in the following order from top to bottom: platelet poor plasma layer, buffy layer, density gradient medium layer (if used), and an erythrocyte/granulocyte layer.

Optionally, an amount of the platelet poor plasma layer can be removed via the swabbable needless injector luer or top coupling element leaving behind the desired volume of the platelet poor plasma layer. Alternatively, all of the platelet poor plasma layer can be retained in the first syringe. A second syringe, e.g., a double syringe, or other second container can be connected to the top coupling element or swabbable needless injector luer. A second syringe (e.g. a double syringe) or second container can have a bottom coupling element. The barrel of the second syringe or second container can comprise a chamber that can hold a biological fluid. The barrel of the second syringe or second container can have a smaller diameter than the first syringe so that the second syringe or second container can fit within the barrel of the first syringe.

All or part of the biological fluid present in the first syringe (e.g., platelet poor plasma layer, buffy layer, density gradient medium layer (if used), and an erythrocyte/granulocyte layer) can be drawn through the top coupling element and into the second syringe or second container. In an example, any remaining platelet poor plasma layer and the buffy layer can be drawn up into the second syringe or other container. The second syringe or second container can be removed and placed into a centrifuge. The second syringe or second container can be centrifuged at any of the soft spin conditions described above for the PRP isolation. Other conditions can include, for example, centrifugation for 3, 5, 7, 10, 15 minutes or more at about 225, 250, 275, 300, 325, 350, 375, 400, 425×g or more. Two layers can be present after centrifugation: a top bone marrow mononuclear cell layer and a bottom erythrocyte/granulocyte layer. The bone marrow mononuclear cell layer can be isolated by, for example, expelling the erythrocyte/granulocyte layer from the bottom coupling element 210 of the second syringe or second container such that the bone marrow mononuclear cell layer is retained in the second syringe. The bone marrow mononuclear cell layer can then be used for direct injection into the patient through an injection set connected to bottom coupling element 210 of the second syringe or second container or can be stored in the second syringe or second container for later use, or removed from the chamber of the second syringe or second container and stored in another container for later use.

Where the second container is a double syringe, such as an Arthrex ACP® double syringe, the inner syringe can be used for easy isolation of bone marrow mononuclear cell layer after the second centrifugation. The plunger of the inner syringe (of the double syringe) is pulled up to isolate the bone marrow mononuclear cell layer after the second centrifugation. Therefore, the inner syringe of the second, double syringe can be used to pull up the bone marrow mononuclear cell layer without disturbing the erythrocyte/granulocyte layer; and the single syringe extrudes out the erythrocyte/granulocyte layer and keeps the bone marrow mononuclear cell layer inside the syringe. The inner syringe of the second syringe can then be removed, a needle can be attached to the bottom coupling element, and the inner syringe of the second, double syringe can be used to directly inject the bone marrow mononuclear cell layer into a patient or container.

The bone marrow mononuclear cell layer can then be used for injection into the patient or can be stored for later use. The bone marrow mononuclear cell layer is similar to the platelet rich plasma layer described above when using whole blood, but additionally contains stem cells.

An embodiment provides methods of adipose tissue fractionation. In an embodiment, purified stromal vascular fraction or layer (SVF) can be isolated from adipose tissue. Adipose tissue can be drawn up into the chamber 130 of a first syringe with a plunger 140 connected to the top coupling element. The adipose tissue can be drawn into the first syringe, either directly from the patient or from a container containing a previously collected sample of adipose tissue. The adipose tissue can be emulsified prior to being drawn into the first syringe or can be mechanically emulsified within the first syringe. The plunger (if used) can be removed from the top coupling element and a swabbable needleless injector luer (or other luer lock port or injector port) can be placed into the top coupling element. FIG. 2A. The first syringe can be placed into a centrifuge and spun under, for example, any of the hard spin centrifuge conditions described above for isolation of PRP. Other centrifuge conditions include, for example, about 400, 500, 600, 666, 700, 800×g or more for about 3, 4, 5, 7, 10 or more minutes. Three layers of biological fluids can be present in the following order from top to bottom: a fatty acid/lipid/oil layer ("the lipid layer"); a compressed adipose layer; and an excess fluid layer (comprising, for example, serous fluid, erythrocytes, and local anesthetic).

The lipid layer can be removed via the swabbable needleless injector luer or top coupling element. The excess fluid layer can be expelled from the bottom coupling element 110, such that the compressed adipose layer is left in the first syringe. About 75, 80, 85, 90, 95, 97, 98, 99 or 100% of the lipid layer and the excess fluid layer are removed. A second syringe (e.g. a double syringe) or second container can be connected to the top coupling element or swabbable needleless injector luer. A second syringe or second container can have a bottom coupling element. The barrel of the second syringe or second container can comprise a chamber that can hold a biological fluid. The barrel of the second syringe or second container can have a smaller diameter than the first syringe so that the second syringe can fit within the barrel of the first syringe.

All or part of the biological fluid present in the first syringe can be drawn through the top coupling element and into the second syringe or second container. In an example, the compressed adipose layer can be drawn up into the second syringe or second container, the second syringe or second container can be removed from the first syringe the second syringe or second container is placed into a centrifuge. The second syringe or second container can be centrifuged under the soft spin conditions described above for PRP isolation. Other conditions include, for example, about 200, 250, 300, 350, 375, 400, 450×g or more for about 3, 4, 5, 7, 10 or more minutes. Two layers can be present after centrifugation: an top adipocyte layer and a bottom stromal vascular layer or fraction. The stromal vascular fraction of adipose tissue is a rich source of preadipocytes, mesenchymal stem cells (MSC), endothelial progenitor cell, T cells, B cells, mast cells, and adipose tissue macrophages. The SVF can be isolated by, for example, expelling it from the bottom luer lock connector of the second syringe or second container. The isolated SVF can then be used for injection into the patient or can be stored for later use.

Platelet Rich Plasma, Bone Marrow Mononuclear Cells, Stromal Vascular Fraction and Uses Thereof In an embodiment, a PRP composition, a BMMC composition, a SVF composition, or other bodily fluids prepared by the methods of disclosed herein can comprise one or more vitamins such as vitamin E, vitamin A, or other retinoids. Vitamins or other retinoids can be present in PRP, BMMC, or SVF at about 40, 30, 20, 10, 5 or less mg/L. Vitamins can provide wound healing and anti-oxidant properties. Alternatively, or additionally, non-vitamin anti-oxidants can be included in the PRP, BMMC, or SVF at about 50, 40, 30, 20, 10, 5, or less mcg/dL. Non-limiting representative examples of such anti-oxidants include β-carotene.

An embodiment provides a composition comprising an autologous platelet rich plasma (PRP) for use in the treatment of soft tissue damage, wherein the PRP comprises about $8×10^6$ to about $1×10^7$ platelets/μL. In an embodiment, the PRP is derived by the methods described herein, and any features relating to PRP produced by methods herein are applicable to the medical use thereof. In an embodiment, the composition comprising an autologous platelet rich plasma (PRP) can be for administration via injection into a ligament, tendon, bone, cartilage, or joint space.

An embodiment provides a composition comprising blood marrow mononuclear cells (BMMC) derived by the methods described herein for use in the treatment of soft tissue injury or damage.

An embodiment provides a composition comprising the stromal vascular fraction (SVF) derived by the methods described herein for use in the treatment of soft tissue injury or damage.

In an embodiment, about 0.1, 0.5, 1, 5, 10, 15, 20, 25 mL or more PRP derived by the methods described herein can be administered to a subject. A subject can be a mammal. A mammal can be human, canine, feline, equine, or bovine.

In an embodiment, PRP, BMMC, or SVF derived by the methods described herein can be administered to a subject not undergoing surgery. PRP, BMMC, or SVF can be administered, such as by an injection, directly into cartilage, ligament, tendons, soft tissue, muscle, or a joint space of a subject not undergoing surgery. For example, a subject having chronic tendinopathies (e.g., Achilles tendinosis, lateral/medial epicondylitis, plantar fasciitis, patellar tendinopathy) can be administered PRP, BMMC, or SVF via injection into a tendon. In an illustrative embodiment, a subject having chondral injuries and early or advanced osteoarthritis can be administered PRP, BMMC, or SVF.

In an embodiment, PRP, BMMC, or SVF derived by the methods described herein can be administered to a subject during surgery. PRP, BMMC, or SVF can be administered during surgery to repair soft tissue damage or injury, such as for a ligament (e.g., anterior cruciate ligament, medical collateral ligament, etc.), cartilage (e.g., meniscus, labrum, etc.), or tendon (e.g., Achilles tendon). PRP, BMMC, or SVF can also be administered during surgery to promote bone repair (e.g., patella, tibia, femur, humerus, etc.). PRP, BMMC, or SVF can also be used to treat ischemia, ischemic stroke, heart injury or damage, muscle injury or damage, osteoarthritis, rheumatoid arthritis, and other diseases. PRP, BMMC, or SVF can be administered directly to soft tissue or to the joint space (e.g., shoulder, knee, ankle, wrist, hip, etc.).

In an embodiment, PRP, BMMC, or SVF derived by the methods described herein can be administered to a subject with a neuropathy (e.g., peripheral neuropathy).

In the methods described herein, the PRP, BMMC, or SVF administered to a subject can be an autologous PRP, BMMC, or SVF. In an embodiment, the PRP, BMMC, or SVF administered to a subject can be an allogeneic PRP, BMMC, or SVF.

In an embodiment, PRP, BMMC, or SVF derived by the methods described herein can be administered in combination with one or more specific growth factors. Growth factors include, but are not limited to, platelet-derived growth factor (PDGF), fibroblast growth factor (FGF), TGF-β (transforming growth factor-β), epithelial growth factor (EGF), and vascular endothelial growth factor (VEGF). Growth factors can be added to the PRP, BMMC, or SVF or administered separately simultaneously or sequentially at about 0.001, 0.01, 0.1, 1.0, 10, 100 or more ng/mL.

In an embodiment, PRP, BMMC, or SVF derived by the methods described herein can be administered in combination with bone marrow concentrate (BMC), bone marrow aspirate (BMA), or lipoaspirate. About 1, 2, 5, 10, 15, 20, 25 mL or more BMC, BMA, or lipoaspirate can be added to the PRP, BMMC, or SVF or separately administered simultaneously or sequentially.

In an illustrative embodiment, PRP, BMMC, or SVF derived by the methods described herein can be administered in combination with stem cells. For example, the PRP, BMMC, or SVF can be administered with mesenchymal stem cells or bone marrow stem cells. About 0.1, 0.5, 1, 2, 5, 10, 15, 20, 25 mL or more mesenchymal stem cells or bone marrow stem cells can be added to the PRP, BMMC, or SVF or separately administered simultaneously or sequentially.

In an embodiment the PRP, BMMC, or SVF derived by the methods herein can be administered directly from the second syringe or second container to the patient through an injection kit attached to the second syringe or second container. For example, where a double syringe is used as the second syringe, the inner syringe can be removed and connected to an injection kit and the PRP, BMMC, or SVF can be directly administered to a patient.

The various considerations set out in respect of PRP, BMMC, or SVF in the preceding paragraphs, and the relevant features relating to administration are all, except for where the context requires otherwise, applicable to the corresponding medical uses of these cell populations as defined herein.

Kits

In an embodiment, a method described herein includes a disposable blood separation kit and apparatus to achieve proper fractionation of the whole blood and collection of the layers. Methods, devices, and device components include monitoring and controlling separation of whole blood and blood components (e.g., a second centrifugation where at least a portion of a PPP has been removed) into fractions and subsequent collection of selected fractions.

Definitions

The terms "buffy layer" or "buffy coat" refer to the middle white layer of white blood cells, platelets, and mesenchymal and/or hematopoietic cells between the plasma layer and the erythrocyte layer following density gradient centrifugation or under hard spin centrifugation conditions of the blood.

The term "platelet poor plasma (PPP)" refers to a top layer of plasma following density gradient centrifugation of the blood or under hard spin centrifugation conditions of the blood. The PPP layer occurs when the centrifugation is at enough force where the white blood cells and platelets fractionate to the buffy layer.

The terms "erythrocyte" and "red blood cell (RBC)" are interchangeable and refer to mature red blood cells.

The term "neutrophil (N)" refers to a type of mature, granulocytic white blood cell. Other granulocytes include basophils and eosinophils.

The term "hard spin" refers to centrifugation conditions that cause erythrocytes to sediment and platelets to sediment in a layer immediately above the erythrocyte layer and below a platelet poor plasma layer. Typically, a hard spin is defined as having a relative centrifugal force (RCF) of about 1500×g to about 2000×g. The term "soft spin" refers to centrifugation conditions that cause erythrocytes to sediment while platelets remain in suspension. Typically, a soft spin is defined as having an RCF of about 20×g to about 200×g.

As used herein, the singular forms "a," "an", and "the" include plural referents unless the context clearly dictates otherwise. The term "about" in association with a numerical value means that the numerical value can vary plus or minus by 5% or less of the numerical value.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The term 'embodiment' as used herein is not intended to limit the invention to any particular combination of features. Any of the embodiments described above and any features referred to that 'can' be or 'may' be present in any embodiment are intended to be combinable in any workable combination with any other or further embodiment or feature described herein.

The following are provided for exemplification purposes only and are not intended to limit the scope of the invention described in broad terms above.

EXAMPLES

Example 1: Preparation of Concentrated Platelet Rich Plasma

A method of producing concentrated platelet rich plasma (i.e., an autologous conditioned plasma) with a higher platelet ratio was developed.

Methods

Whole blood was drawn into a syringe (each of three different donors). The plunger was removed from the syringe, and the whole blood was centrifuged (Hettich® 1390 bucket, Hettich Lab Technology, Beverly, Mass.)) in the syringe at 1705×g for 10 minutes at room temperature. Three fractions were discernible—a top yellowish clear fraction (platelet poor plasma), a white interface fraction (the "buffy layer"), and a red fraction at the bottom of the syringe. Approximately 20 mL of the platelet poor plasma fraction was removed. The remaining plasma and buffy layers were transferred to an Arthrex ACP® double-syringe system (Arthrex Inc., Naples, Fla.). The double syringe connected to the larger syringe via a swabbable, needleless Luer-Lok® connection. The double syringe was placed in a Hettich® 1390 bucket and centrifuged at 41.65×g for 5 minutes at room temperature. Following centrifugation, two fractions were discernible—an upper, yellowish clear fraction (platelet rich plasma) and a bottom red erythrocyte fraction. The upper fraction was isolated using the inner syringe of the Arthrex ACP® double-syringe. The total volume of PRP processed for measurements of cellular content was 6 m L.

Results

The whole blood (WB) and the final PRP fraction were analyzed for cellular content.

TABLE 1

Components of WB and PRP from 3 Donors.

| Component | Donor 1 | | Donor 2 | | Donor 3 | |
|---|---|---|---|---|---|---|
| | WB | PRP | WB | PRP | WB | PRP |
| White Blood Cells[a] | 6.18 | 3.30 | 2.98 | 0.55 | 3.58 | 1.90 |
| Red Blood Cells[b] | 4.45 | 0.15 | 5.07 | 0.05 | 4.48 | 0.06 |
| Hematocrit | 38.8% | 0.7% | 48.4% | 0.2% | 42.8% | 0.5% |
| Platelets[c] | 176 | 835 | 125 | 874 | 354 | 990 |
| Mean Platelet Volume[d] | 11.0 | 11.0 | 11.6 | 9.0 | 8.1 | 7.6 |
| Neutrophils[e] | 2.98 | 0.01 | 1.83 | 0.23 | 1.44 | 0.12 |

[a] $10^3/\mu L$;
[b] $10^6/\mu L$;
[c] $10^3/\mu L$;
[d] fL;
[e] $10^3/\mu L$

The components are compared in Table 2 as a ratio of amount of the component (white blood cells (WBC), red blood cells (RBC), platelets (PLT), and neutrophils (N)) in the PRP as compared to the whole blood.

TABLE 2

Cellular ratios of PRP to Whole Blood

| Ratios | Donor 1 | Donor 2 | Donor 3 | Average |
|---|---|---|---|---|
| WBC Ratio | 0.53 | 0.18 | 0.53 | 0.42 |
| RBC Ratio | 0.03 | 0.01 | 0.01 | 0.02 |
| PLT Ratio | 4.47 | 6.99 | 2.80 | 4.84 |
| N Ratio | <0.01 | 0.13 | 0.08 | 0.07 |

The method described herein produced a PRP with an increased high platelet ratio and decreased white blood cell, red blood cell, and neutrophil ratios.

Example 2: Comparison of Concentrated PRPs

Concentrated PRPs were generated by different methods to compare with the concentrated PRP generated in Example 1.

Methods

Concentrated PRPs were prepared by the Arthrex ACP® double syringe system and Angel® PRP systems (Arthrex Inc., Naples, Fla.) according to the manufacturer's instructions. Three separate Angel® PRPs were prepared with the only difference being a 2%, 7%, and 15% hematocrit setting.

Results

The components of the PRP prepared by various different methodologies are compared in Table 3 (PRP to whole blood) (see, also, FIG. 1). Similar to Example 1, each Angel® PRP sample processed for measurements of cellular content was 6 mL. However, the Arthrex ACP® double syringe system sample processed for measurements of cellular content was 4.6 mL. The data were extrapolated from 4.6 mL to 6.0 mL to provide a comparison with the same volumes.

TABLE 3

Cellular ratios of PRP to Whole Blood

| Ratios | Example 1 | Arthrex ACP® | Angel® @ 2% | Angel® @ 7% | Angel® @ 15% |
|---|---|---|---|---|---|
| WBC Ratio | 0.42 | 0.41 | 0.38 | 1.43 | 2.06 |
| PLT Ratio | 4.84 | 1.90 | 2.93 | 4.17 | 4.94 |
| RBC Ratio | 0.02 | 0.01 | 0.05 | 0.10 | 0.30 |
| N Ratio | 0.07 | 0.05 | 0.18 | 0.72 | 1.15 |

The method of Example 1 produced a PRP with a higher platelet ratio than the other methods except for the Angel® PRP sample with a 15% hematocrit. However, the red blood cell, neutrophil and white blood cell ratios were much lower than the Angel® PRP sample with a 15% hematocrit.

The invention claimed is:

1. A method of blood fractionation comprising:
   a) centrifuging whole blood in a first syringe having a top coupling element and a bottom coupling element, wherein the whole blood fractionates into a platelet poor plasma layer, a buffy layer, and an erythrocyte layer within the syringe;
   b) removing at least a portion of the platelet poor plasma layer from the top coupling element of the first syringe;
   c) attaching a bottom coupling element of a second syringe or second container to the top coupling element of the first syringe;
   d) drawing any of the platelet poor plasma layer, the buffy layer, and optionally part of the erythrocyte layer into the second syringe or second container; and
   e) centrifuging the second syringe or second container wherein the any of the platelet poor plasma layer, the buffy layer, and the erythrocyte layer fractionates into a platelet rich plasma layer and an erythrocyte layer.

2. The method of claim 1, wherein the platelet rich plasma layer is removed and transferred to a container.

3. The method of claim 1, wherein the platelet rich plasma layer comprises about $8 \times 10^6$ to about $1 \times 10^7$ platelets/$\mu L$.

4. The method of claim 1, wherein the platelet rich plasma layer comprises about $0.1 \times 10^5$ to about $2 \times 10^5$ erythrocytes/$\mu L$.

5. The method of claim 1, wherein the platelet rich plasma layer comprises about 500 to about 4000 white blood cells/$\mu L$.

6. The method of claim 1, wherein the platelet rich plasma layer comprises about 10 to about 300 neutrophils/$\mu L$.

7. The method of claim 1, wherein the centrifuging in step (a) has a relative centrifugal force (RCF) of about 1500×g to about 2000×g.

8. The method of claim 1, wherein the centrifuging in step (e) has a relative centrifugal force (RCF) of about 30×g to about 200×g.

9. The method of claim 1, wherein the second syringe is a double syringe.

10. The method of claim 9, wherein the double syringe comprises an outer syringe having a first body with a first diameter; and an inner syringe having a second body with a second diameter smaller than the first diameter, the outer syringe being in direct fluid communication with the inner syringe, and the inner syringe being located within the distal outer syringe.

11. The method of claim 10, wherein the inner syringe comprises a plunger, and wherein the plunger of the inner syringe is pulled up to isolate the platelet rich plasma after the second centrifugation without disturbing the erythrocyte layer.

12. The method of claim 11, wherein the inner syringe is removed from the outer syringe and a needle is attached to a bottom coupling element of the inner syringe.

13. The method of claim 12, further comprising injecting the platelet rich plasma from the inner syringe directly into a patient or container.

14. The method of claim 1, further comprising expelling the erythrocyte layer from the second syringe or second container and retaining the platelet rich plasma in the second syringe or second container.

15. The method of claim 14, further comprising attaching a needle to the bottom coupling element of the second syringe or second container.

16. The method of claim 15, further comprising injecting the platelet rich plasma of the second syringe into a ligament, tendon, bone, cartilage, or joint space of a patient.

* * * * *